(12) United States Patent
Van Houwelingen

(10) Patent No.: US 8,834,379 B2
(45) Date of Patent: Sep. 16, 2014

(54) INDICATOR FOR FLUID RESUSCITATION

(75) Inventor: Marc Van Houwelingen, Rotterdam (NL)

(73) Assignee: Dräger Medical GmbH, Lübeck (DE)

( * ) Notice: Subject to any disclaimer, the term of this patent is extended or adjusted under 35 U.S.C. 154(b) by 405 days.

(21) Appl. No.: 13/071,983

(22) Filed: Mar. 25, 2011

(65) Prior Publication Data
US 2011/0237959 A1 Sep. 29, 2011

(30) Foreign Application Priority Data
Mar. 26, 2010 (EP) .................................... 10158025

(51) Int. Cl.
| | | |
|---|---|---|
| *A61B 5/08* | (2006.01) | |
| *A61M 16/00* | (2006.01) | |
| A61B 5/087 | (2006.01) | |
| A61B 5/091 | (2006.01) | |
| A61B 5/021 | (2006.01) | |

(52) U.S. Cl.
CPC ................ *A61M 16/00* (2013.01); *A61B 5/087* (2013.01); *A61M 16/0084* (2014.02); *A61B 5/091* (2013.01); *A61B 5/021* (2013.01); *A61B 5/0816* (2013.01)
USPC ........... 600/484; 600/481; 600/485; 600/529; 600/533; 600/534; 600/538

(58) Field of Classification Search
USPC .......................... 600/484, 533, 529, 485, 481; 128/200.24, 200.18, 204.23
See application file for complete search history.

(56) References Cited

U.S. PATENT DOCUMENTS

| | | | |
|---|---|---|---|
| 5,769,082 A | * | 6/1998 | Perel .............................. 600/484 |
| 5,980,463 A | | 11/1999 | Brockway et al. |
| 6,138,675 A | * | 10/2000 | Berthon-Jones ......... 128/204.23 |
| 2002/0020414 A1 | * | 2/2002 | Fukunaga ................ 128/205.13 |
| 2004/0260186 A1 | | 12/2004 | Dekker |
| 2012/0179061 A1 | * | 7/2012 | Ramanan et al. ............. 600/538 |

FOREIGN PATENT DOCUMENTS

| | | |
|---|---|---|
| DE | 102007024072 A1 | 11/2007 |
| WO | WO 2009/096820 A1 | 8/2009 |

* cited by examiner

*Primary Examiner* — Michael Kahelin
*Assistant Examiner* — Tho Tran
(74) *Attorney, Agent, or Firm* — McGlew and Tuttle, P.C.

(57) ABSTRACT

A system for providing an indication of cardiovascular function, includes a respiration input (1) for receiving a respiration-related signal indicative of a physical property of respiration gases administered to a patient. A hemodynamic input (2) is provided for receiving a hemodynamic-related signal indicative of a hemodynamic property. An inspiration detector (3) is provided for processing the respiration-related signal to detect times of inspiration and a measure of the size of the inspiration. A correlator (5) is provided for correlating the sizes of inspiration with the hemodynamic-related signal, to obtain the indication of cardiovascular function. The respiration-related signal is indicative of inspiration pressure, inspiration volume, or inspiration flow. The hemodynamic-related signal is indicative of blood pressure.

19 Claims, 5 Drawing Sheets

INDICATOR FOR FLUID RESUSCITATION

CROSS REFERENCE TO RELATED APPLICATIONS

This application claims the benefit of priority under 35 U.S.C. §119 of European Patent Application EP 10 158 025.6 filed Mar. 26, 2010, the entire contents of which are incorporated herein by reference.

FIELD OF THE INVENTION

The invention relates to a system for providing an indication of cardiovascular function. The invention further relates to a method of providing an indication of cardiovascular function. The invention further relates to a computer program product for providing an indication of cardiovascular function.

BACKGROUND OF THE INVENTION

In the critical care department of a hospital, there are patients that are seriously ill and of whom the cardiovascular function needs continuous attention. Often these patients also are mechanically ventilated, either continuously or during surgery. The monitoring of the cardiovascular status of these patients is done by continuous measurement of the blood pressure and the heart rate. These parameters, however, are often not accurate enough to follow the cardiovascular function in time and to make a good statement about the significance of the changes.

Therefore other methods have been developed, based on mandatory mechanical ventilation. One of the known methods is the "respiratory systolic variation test" (RSVT). The RSVT is a measure of the slope of the decrease in the systolic arterial blood pressure in response to a standardized maneuver consisting of a series of successive incremental pressure-controlled breaths. Such a method is described in U.S. Pat. No. 5,769,082 by Perel. The procedure as proposed in U.S. Pat. No. 5,769,082 can be described as follows. The patient is ventilated by a mechanical ventilator in a mandatory ventilation mode, such as Volume Controlled Mandatory Ventilation (VCCMV) or Pressure Controlled Mandatory Ventilation (PC-CMV). In order to measure the cardiovascular status a respiratory maneuver is made. A sequence of consecutive tidal volumes of increasing magnitude is applied to the ventilated patient. These varying pressures cause a reaction of the cardiovascular system.

U.S. Pat. No. 5,769,082 further discloses a short apnea period before the series of tidal volumes with varying magnitude is applied. This may be done to have a more significant effect of the variation in pressure. FIG. 1A illustrates an example of measured blood pressure values in mm Hg, and FIG. 1B illustrates an example the airway pressure in cm $H_2O$, both as a function of time. T1 to T2 indicates the apnea period. From T2 to T3, the airway pressure of successive tides is increased; as a consequence, the higher blood pressure increases whereas the lower blood pressure decreases. The slope of a line connecting the lower blood pressures is determined in the RSVT.

SUMMARY OF THE INVENTION

It would be advantageous to have an improved system for providing an indication of cardiovascular function. To better address this concern, a first aspect of the invention provides a system comprising a respiration input for receiving a respiration-related signal indicative of a physical property of respiration gases administered to a patient; a hemodynamic input for receiving a hemodynamic-related signal indicative of a hemodynamic property; an inspiration detector for processing the respiration-related signal to detect times of inspiration and a measure of the size of the inspiration; and a correlator for correlating the sizes of inspiration with the hemodynamic-related signal, to obtain the indication of cardiovascular function.

Because the system detects the times of inspiration based on the physical property, the exact time of the start of each breath does not have to be provided as a separate signal from the mechanical ventilator. Consequently, the mechanical ventilator and the system for providing an indication of cardiovascular function do not have to communicate with each other directly. For example, the respiration-related signal may be measured separately. If the respiration-related signal is generated by the mechanical ventilator, the mechanical ventilator only needs to supply the airway pressure signal, whereas a specific indication when each inspiration starts or when a sequence of increasing pressures begins is not needed. Moreover, by correlating the sizes of inspiration with the hemodynamic-related signal, it is not necessary to use a predetermined, machine initiated sequence of increasing airway pressures or increasing tidal volumes. In contrast, the airway pressures or tidal volumes do not need to be monotonically increasing and can vary randomly. Because of this, it becomes possible to provide the indication of cardiovascular function also when manually operated mechanical ventilation is used, for example using a handbag (hand air pump). Moreover, it becomes possible to provide the indication of cardiovascular function without mandatory breathing, for example by measuring airflow of spontaneous breathing. The times of inspiration may include the beginning of an inspiration and/or the end of an inspiration.

The respiration-related signal may be indicative of inspiration pressure, inspiration volume, or inspiration flow. These quantities may be correlated with the hemodynamic property to obtain the indication of cardiovascular function. The inspiration flow may be converted into inspiration volume before performing the correlation.

The hemodynamic-related signal may be indicative of blood pressure. This is an important example of a hemodynamic-related signal. However, another hemodynamic property may be used.

The system may comprise a variance detector for determining a variance in the size of inspiration of successive inspirations, and a threshold means for comparing the variance of the size of inspiration with a threshold, wherein the correlator is arranged for obtaining the indication of cardiovascular function only if the variance exceeds the threshold. This way, the accuracy of the indication of cardiovascular function is improved.

The system may be arranged for automatically performing the processing, determining, and correlating based on newly received data while the respiration related signal and the hemodynamic-related signal are being received. This way the indication of cardiovascular function is updated on-line as the signals are received, for example after every breath. This may be applied to obtain live information during ventilation of a patient.

The system may comprise a display for displaying the indication of cardiovascular function. This is a convenient way to convey the indication to a user.

The system may be arranged for handling a respiration-related signal indicative of non-monotonically varying sizes of the inspiration in successive inspirations. The inspiration detector may detect times of inspiration and a measure of the size of the inspiration, regardless of the actual sizes of the inspiration in successive tides. The correlator may correlate the sizes of inspiration with the hemodynamic-related signal regardless of the order in which the inspiration sizes were applied. This makes the system easier to use, because random variations in tidal volume or pressure may be applied.

The system may comprise a device comprising a blood pressure sensor for generating the hemodynamic-related signal and a respiration sensor for generating the respiration-related signal, wherein the respiration sensor is arranged for being in fluid communication with a connector for connecting a measurement hose. This way, both measurements can be combined in a single device. In this way, the system for providing an indication of cardiovascular function can operate independently from any other equipment.

Another aspect of the invention provides a device for providing mechanical ventilation to a patient, comprising a handbag for manually administering air to a patient and a respiration-related sensor for generating a respiration-related signal indicative of a physical property of respiration gases administered to a patient, wherein the respiration-related signal is suitable for being received and processed by the system for providing an indication of cardiovascular function. This is useful, for example in emergency situations where an electrical mechanical ventilator is not available. However, the use of a handbag is not a limitation. For example, a mechanical ventilator may be used which allows a doctor to manually change tidal volume or airway pressure. It is not necessary to use a mechanical ventilator which can be pre-programmed to perform a particular sequence of tidal volumes or pressures.

Another aspect of the invention provides a method of providing an indication of cardiovascular function, comprising receiving a respiration-related signal indicative of a physical property of respiration gases administered to a patient; receiving a hemodynamic-related signal indicative of a hemodynamic property; processing the respiration-related signal to detect times of inspiration and a measure of the size of the inspiration; and correlating the sizes of inspiration with the hemodynamic-related signal, to obtain the indication of cardiovascular function.

Another aspect of the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

These and other aspects of the invention are apparent from and will be elucidated with reference to the embodiments described hereinafter. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
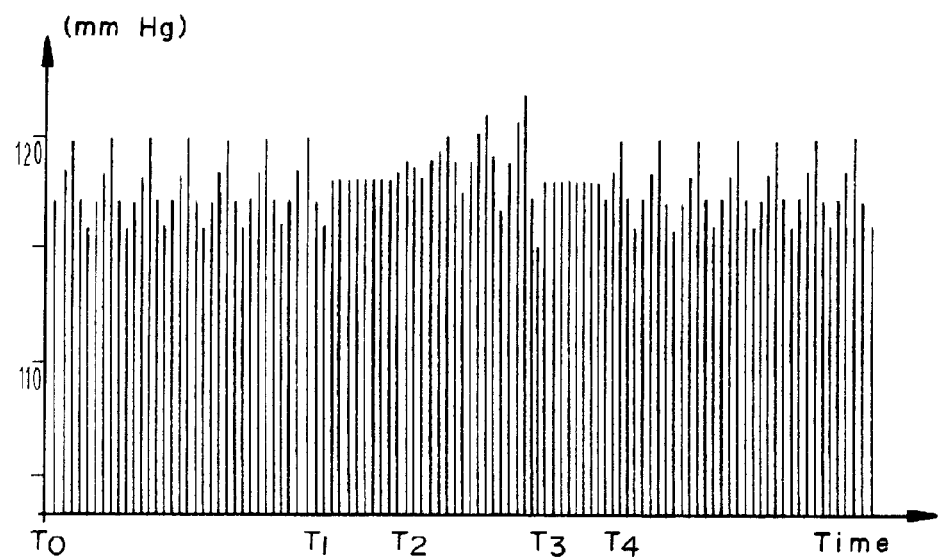
FIG. 1A is a graph of blood pressure versus time.
Figure 1B:
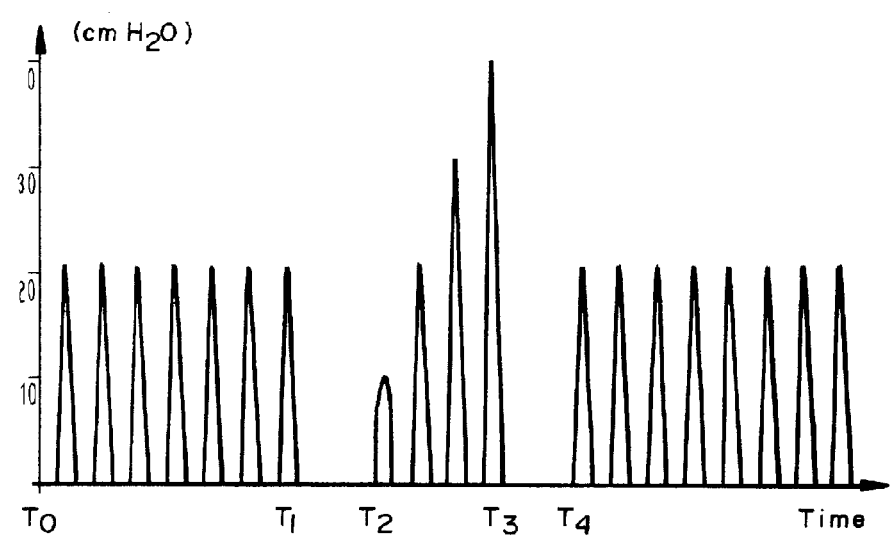
FIG. 1B is a graph of airway pressure versus time.

Referring to the drawings in particular, FIG. 1A and FIG. 1B illustrate hemodynamic and respiratory data which may occur during the use of the method disclosed in U.S. Pat. No. 5,769,082. FIG. 1B illustrates an example of the airway pressure applied by a mechanical ventilator in cm $H_2O$, as a function of time. T1 to T2 indicates the apnea period. From T2 to T3, the airway pressure of successive tides is increased. FIG. 1A illustrates an example of blood pressure values in mm Hg as a function of time, measured during the mechanical ventilation pattern of FIG. 1B. It can be seen in the interval from T2 to T3, that blood pressure variance increases as a result of the increasing airway pressure. In this interval, the higher blood pressure increases whereas the lower blood pressure decreases. The slope of a line connecting the lower blood pressures may be determined in the RSVT.

Figure 2A:
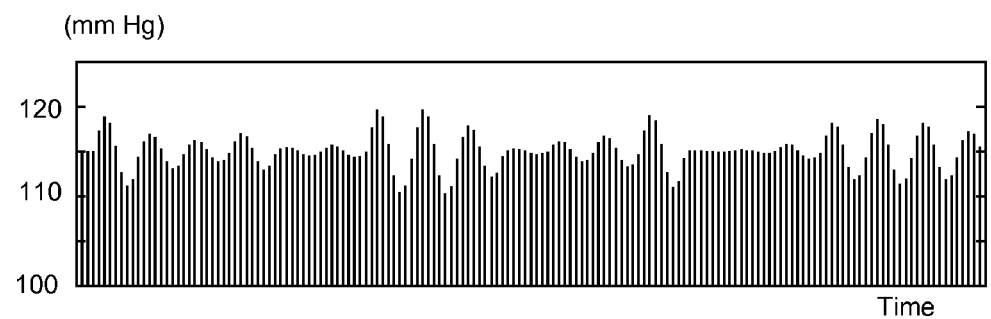
FIG. 2A is a graph of blood pressure versus time.
Figure 2B:
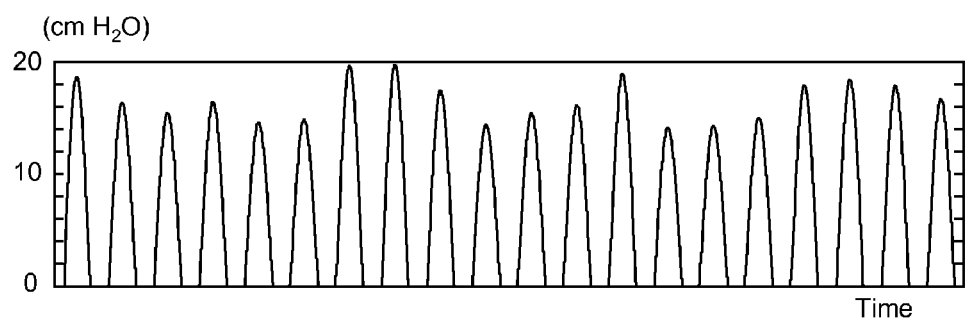
FIG. 2B is a graph of airway pressure versus time.

FIG. 2A and FIG. 2B illustrate an example of hemodynamic and respiratory data which may occur when supplying a variable amount of air to the patient in different breath cycles. FIG. 2B illustrates an example of airway pressure applied in cm $H_2O$, as a function of time. As is apparent from the graph, different airway pressure levels have been applied in different inspirations. FIG. 2A illustrates an example of arterial systolic pressures as a function of time, occurring as a response to the ventilation pattern of FIG. 2B. It can be observed from these figures, that larger airway pressure values result in larger variance in arterial systolic blood pressure values; the higher values increase whereas the lower values decrease.

Figure 2C:
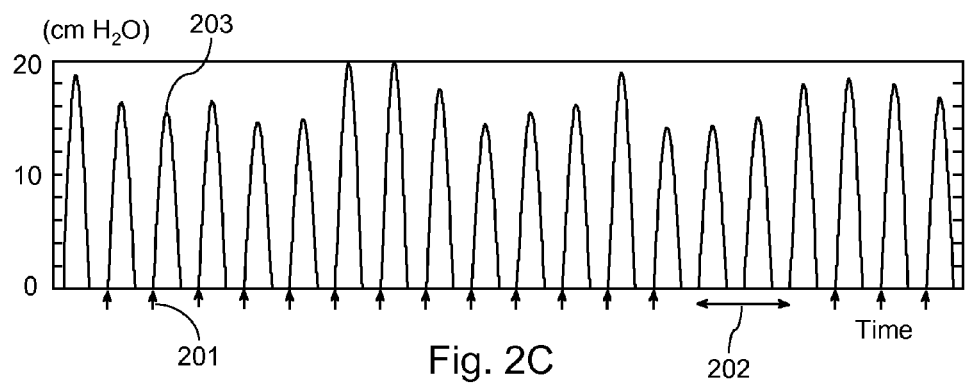
FIG. 2C is a graph of airway pressure versus time.

FIG. 2C shows the same graph as FIG. 2B. However, in FIG. 2C, example moments are indicated with arrows 201. At these moments, the data collected so far may be analyzed to compute an indication of cardiovascular function. However, this is not a limitation. This indication may also be computed at other moments. Interval 202 is an example of an interval with relatively little airway pressure variation. In such an interval, the computation of the indication of cardiovascular function may be suspended, because the reliability of the indication may depend on the variation of the airway pressure level.

Figure 3:
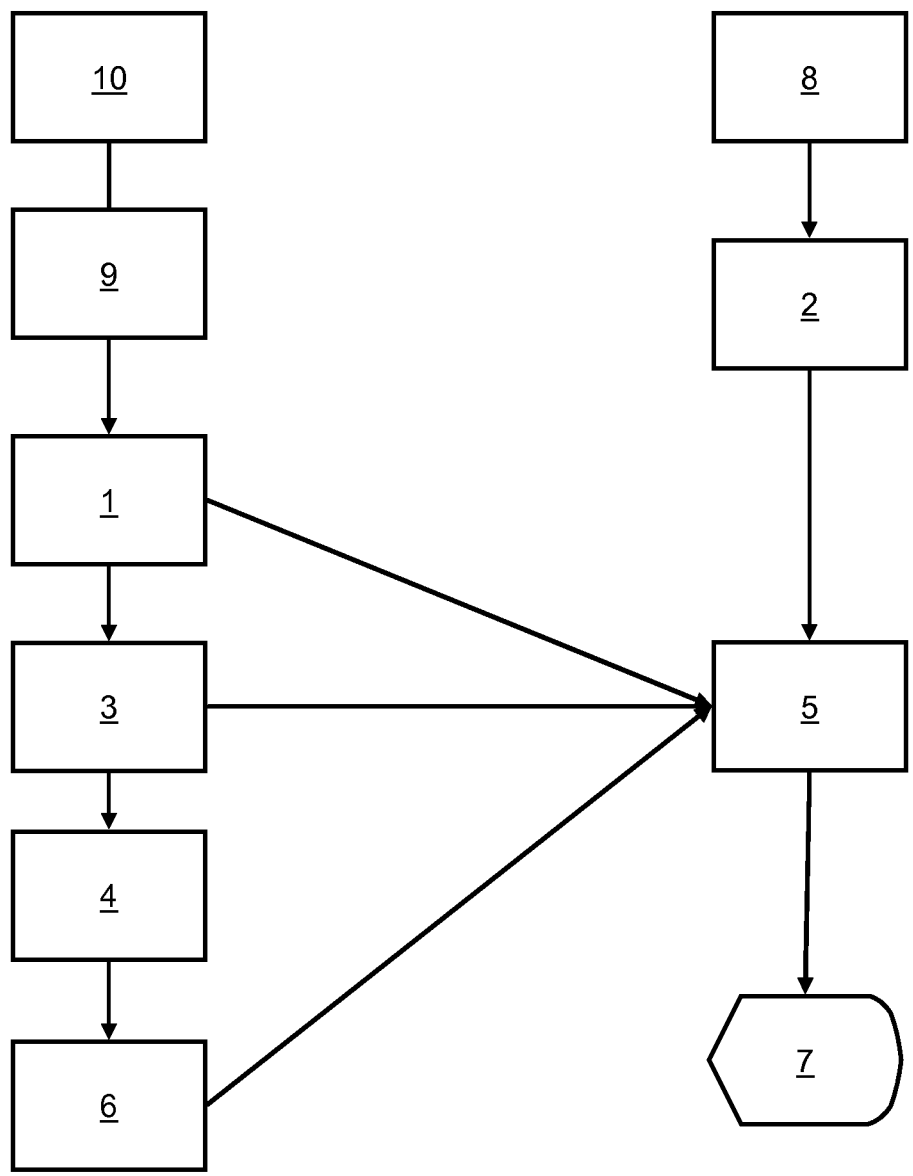
FIG. 3 is a diagram of a system for providing an indication of cardiovascular function.

FIG. 3 illustrates elements of a system for providing an indication of cardiovascular function. The system may be incorporated into a medical monitoring device, such as a blood pressure monitoring device or a mechanical respirator. At least part of the system may be implemented as software, for example embedded software of a medical monitoring device. Alternatively, at least part of the system may be implemented as a software program for a computer workstation. The system may also be implemented at least in part by means of a dedicated electronic circuit.

The system may comprise a respiration input 1 for receiving a respiration related signal. This signal may be indicative of a physical property of respiration gases administered to a patient. For example, the respiration-related signal is indicative of inspiration pressure, inspiration volume, or inspiration flow. The respiration-related signal may be received from an external sensor, which may be located along the patient circuit of a mechanical ventilator. The respiration input may be arranged for receiving the signal in electric form. Such an electric signal may be generated by the external sensor. Alternatively, a respiration-related sensor 9 may be built into the system and fluidly connected to the airway passage via a connector 10.

The system may further comprise a hemodynamic input 2 for receiving a hemodynamic-related signal indicative of a hemodynamic property or parameter. The hemodynamic-related signal may be indicative of blood pressure, for example arterial blood pressure. However, other hemodynamic properties may also be used. For example, it can be arterial distension as measured by ultrasound, applanation tonometry, or any other hemodynamic parameter. Such measurements may result in a detailed monitoring of a patient in a critical phase.

The hemodynamic-related signal may be obtained from an external hemodynamic-related sensor device, or from a built-in hemodynamic-related sensor 8. The signal may be an electric signal or have another suitable form.

The system may further comprise an inspiration detector 3. The inspiration detector 3 receives the respiration-related signal from the respiration input 1 and processes the respiration-related signal to detect times of inspiration and a measure of the size of the inspiration. Suitable signal processing methods for performing this kind of processing are available to the person skilled in the art. An example time of inspiration is depicted at 201 in FIG. 2C. An example of the size of an inspiration is depicted at 203 in the same figure, as the maximum pressure during an inspiration maneuver. However, another way of determining the size of an inspiration may also be used, for example the tidal volume or the average pressure during an inspiration maneuver. Also, the times of expiration may be determined.

The system may comprise a variance detector 4 for determining a variance in the size of inspiration of successive inspirations. This variance, may be any measure indicative of variability of the sizes of inspirations in a given time span. This time span may span a time interval of a given duration which ends at the latest available respiration-related signal data. The variance may, for example, be the maximal difference between any two sizes or the standard deviation of the sizes.

The system may comprise a correlator 5 for correlating the sizes of inspiration with the hemodynamic-related signal, to obtain the indication of cardiovascular function. For example, a linear regression model may be fitted with the sizes of inspiration and the highest or lowest systolic arterial pressure measured in an interval shortly after the respective inspirations. The slope of the regression model may be used as an indication of cardiovascular function. However, this is not a limitation. Other kinds of correlation may be determined. Also, other signals may be used instead of systolic arterial pressure, including for example arterial distension as described above.

The system may comprise a threshold means 6. This threshold means 6 may receive the variance in the size of inspiration from the variance detector 4. The threshold means 6 may compare the variance with a threshold. This threshold may be configured such that the comparison is an indication whether a sufficiently accurate indication of cardiovascular function may be obtained from the available signals. For example, it may be difficult to accurately determine the slope of the regression model which may be fitted by the correlator 5 if the sizes of inspiration are all about the same. Consequently, the correlator 5 may be arranged for computing the indication of cardiovascular function only if the variance exceeds the threshold.

The system may be arranged for automatically performing the processing, determining, and correlating based on newly received data while the respiration related signal and the hemodynamic-related signal are being received. To that end, inputs 1 and 2 may continuously monitor the incoming signal, and forward it to the other modules, in order to update the indication of cardiovascular function, as long as the variance remains above the threshold.

The system may comprise a display 7 for displaying the indication of cardiovascular function. The display may have the form of a numeric indication, for example. It is also possible to provide an alarm if it is detected that the cardiovascular function deteriorates. Such an alarm may be visual and/or audible.

The system is capable of handling a respiration-related signal indicative of nonmonotonically varying sizes of the inspiration in successive inspirations. Also, any specific trigger for starting the computations is not necessary, because the system can analyze the respiration-related signal and determine automatically the beginning of a respiratory cycle and select automatically, after a few respiratory cycles, a plurality of respiratory cycles and corresponding hemodynamic-related signal values to be used in the computation of the indication of cardiovascular function. However, a user interface element may be provided for enabling or disabling the functionality of computing the indication of cardiovascular function.

The system may comprise a device comprising a blood pressure sensor 8, coupled to the hemodynamic input 2, for generating the hemodynamic-related signal. Moreover, the device may comprise a respiration sensor 9, coupled to the respiration input 9, for generating the respiration-related signal. The respiration sensor 9 may be fluidly connected with a connector 10 for connecting one end of a measurement hose. Another end of this measurement hose may be connected to the airway passage. The device with these two sensors may also comprise other parts of the system for providing an indication of cardiovascular function. For example, the whole system depicted in FIG. 3 may be implemented in a single device. This device may comprise a mechanical ventilator and/or a hemodynamic monitoring device.

Figure 4A:
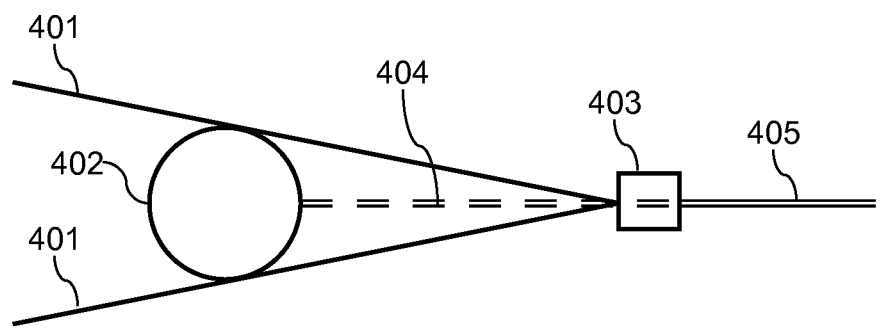
FIG. 4A is a simplified diagram of a device for providing mechanical ventilation to a patient.
Figure 4B:
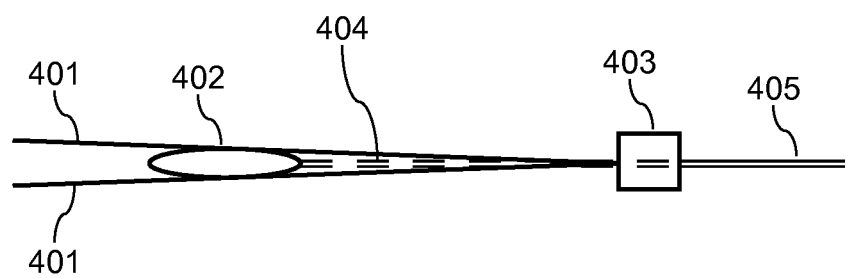
FIG. 4B is a simplified diagram of a device for providing mechanical ventilation to a patient, in a compressed state.

FIG. 4A shows a simplified diagram of a device for providing mechanical ventilation to a patient, comprising a handbag 402 for manually administering air to a patient. Handles 401 may be used to compress and decompress the handbag 402. FIG. 4B shows the device in compressed state. In FIGS. 4A and 4B, similar elements have been indicated by the same reference numerals. The device comprises an airway 404,405 for transporting gases to a patient. Along the airway 404,405, the device comprises a respiration-related sensor 403 for generating a respiration related signal indicative of a physical property of respiration gases administered to a patient. This signal may be forwarded to the respiration input 1 of the system for providing an indication of cardiovascular function.

Figure 5:
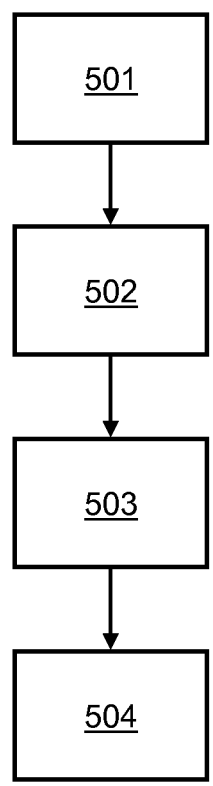
FIG. 5 is a flowchart illustrating a method of providing an indication of cardiovascular function.

FIG. 5 shows a flowchart of a method of providing an indication of cardiovascular function. The method comprises a step 501 of receiving a respiration related signal indicative of a physical property of respiration gases administered to a patient. The method comprises a step 502 of receiving a hemodynamic-related signal indicative of a hemodynamic property. The method comprises a step 503 of processing the respiration-related signal to detect times of inspiration and a measure of the size of the inspiration. The method comprises a step 504 of correlating the sizes of inspiration with the hemodynamic-related signal, to obtain the indication of cardiovascular function. The method may be implemented in software as a computer program product. The method and computer program product may be extended with other functionality, for example as described for the system in respect of FIG. 3.

The following example illustrates the use of this method and/or system. If a patient has had an accident on the street the rescuers may arrive with a handbag, a blood pressure sensor and maybe other lightweight, easy to operate equipment. They may measure the blood pressure of the patient continuously and at the same time they may ventilate the patient with a handbag. However, using this kind of equipment, it is not possible or difficult to accurately supply a fixed or predetermined tidal volume. More likely, the tidal volume will be different and to some extend random for each ventilation stroke of the handbag. When the actual tidal volume or airway pressure is measured, it can be correlated with the blood pressure measurements for a series of for example 4 ventilation strokes. From a small knowledge database the rescuer can see to what degree fluid resuscitation is needed, and he or she can take the necessary action based on this information.

For example, this method can be used with a small, lightweight modification of the handbag. The handbag may be extended with a pressure (or a flow) sensor and a controller with a small display. This can be either built into the handbag or it can be added as an accessory to the handbag. The advantage of this modified handbag is that the rescuer does not need to carry a bulky and heavy ventilator (which may employ an electrical blower or compressed air) to support his or her actions.

While applying such a sequence of ventilation pressures, a hemodynamic parameter may be measured. This hemodynamic parameter may comprise the arterial pressure. However, other hemodynamic properties may also be used. For example, it can be arterial distension as measured by ultrasound, applanation tonometry or any other hemodynamic parameter. Such measurements can result in a very detailed monitoring of a patient in a critical phase.

The techniques described herein may also be applied to patients that still have some spontaneous but irregular breathing. Such an irregular breathing results in variable airway pressures and tidal volumes. The airway pressures and/or tidal volumes thus obtained could be measured and correlated with a continuous blood pressure measurement. This way, an indication of cardiovascular function, for example information about the need for fluid resuscitation, may be obtained. This may avoid the need for a patient to undergo stressful mechanical ventilation.

The pressure variations that are the result of, for example, the ventilation of a patient with a handbag or a patient's autonomous breathing, are measured. These variations are correlated with a hemodynamic measurement. For this purpose a hemodynamic measurement may be performed, such that corresponding measurements of respiration-related quantity and hemodynamic-related quantity, measured at the same time, are obtained. Moreover, a display may be provided to inform the user of the result of the correlation.

The respiration-related property, indicative of a physical property of respiration gases administered to a patient, described herein, may relate to airway pressure, tidal volume and/or airway flow. However, this is not a limitation. Other respiration related properties, such as $O_2$ and $CO_2$ content, are also possible and can be correlated with the hemodynamic-related property.

The techniques described herein do not need a mechanical ventilator capable of being programmed to make a series of well-defined pressure steps after a short apnea period. Consequently, a less complex mechanical ventilator can be used. This makes the system more portable and/or more useful in emergency situations. Moreover, the system can be used without mechanical ventilation if the patient breathes autonomously. In the latter case, for example the tidal volumes may be measured.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

While specific embodiments of the invention have been shown and described in detail to illustrate the application of the principles of the invention, it will be understood that the invention may be embodied otherwise without departing from such principles.

What is claimed is:

1. A system for providing an indication of cardiovascular function, the system comprising:
    a respiration input for receiving a respiration-related signal indicative of a physical property of respiration gases administered to a patient;
    a hemodynamic input for receiving a hemodynamic-related signal indicative of a hemodynamic property;
    an inspiration detector for processing the respiration-related signal to detect times of inspiration and a measure of a size of inspiration;
    a correlator for correlating the sizes of inspiration with the hemodynamic-related signal, to obtain the indication of cardiovascular function;
    a variance detector for determining a variance in the size of inspiration of successive inspirations; and
    a threshold means for comparing the variance of the size of inspiration with a threshold, wherein the correlator obtains the indication of cardiovascular function only if the variance exceeds the threshold.

2. A system according to claim 1, wherein the respiration-related signal is indicative of inspiration pressure, inspiration volume, or inspiration flow.

3. A system according to claim 1, wherein the hemodynamic-related signal is indicative of blood pressure.

4. A system according to claim 1, wherein the system automatically performs the processing, the determining, and the correlating based on newly received data while the respiration-related signal and the hemodynamic-related signal are being received.

5. A system according to claim 1, further comprising a display for displaying the indication of cardiovascular function.

6. A system according to claim 1, wherein the system handles a respiration-related signal indicative of nonmonotonically varying sizes of the inspiration in successive inspirations.

7. A system according to claim 1, further comprising:
    a device comprising a blood pressure sensor for generating the hemodynamic-related signal and a respiration sensor for generating the respiration-related signal, wherein the respiration sensor is in fluid communication with a connector for connecting a measurement hose.

8. A system according to claim 1, wherein said variance corresponds to a variability of sizes of said successive inspirations in a given time span, said comparison of said variance of said size of inspiration with said threshold providing an indication as to whether an accurate cardiovascular function is obtainable from said respiration-related signal and said hemodynamic-related signal.

9. A device for providing mechanical ventilation to a patient, the device comprising
    a handbag for manually administering air to a patient;
    a respiration related sensor for generating a respiration-related signal indicative of a physical property of respiration gases administered to a patient, wherein the respiration-related signal is for a system for providing an indication of cardiovascular function, the system comprising a respiration input for receiving the respiration-related signal indicative of a physical property of respiration gases administered to a patient, a hemodynamic input for receiving a hemodynamic-related signal indicative of a hemodynamic property, an inspiration detector for processing the respiration-related signal to detect times of inspiration and a measure of a size of inspiration and a correlator for correlating the sizes of inspiration with the hemodynamic-related signal, to obtain the indication of cardiovascular function, said system further comprising a variance detector for determining a variance in the size of inspiration of successive inspirations and a threshold means for comparing the variance of the size of inspiration with a threshold, wherein the correlator obtains the indication of cardiovascular function only if the variance exceeds the threshold.

10. A device according to claim 9, wherein the respiration-related signal is indicative of inspiration pressure, inspiration volume, or inspiration flow.

11. A device according to claim 10, wherein the hemodynamic-related signal is indicative of blood pressure.

12. A device according to claim 11, wherein the system automatically performs the processing, the determining, and the correlating based on newly received data while the respiration-related signal and the hemodynamic-related signal are being received.

13. A device according to claim 12, further comprising a display for displaying the indication of cardiovascular function.

14. A device according to claim 12, wherein the system handles a respiration-related signal indicative of nonmonotonically varying sizes of the inspiration in successive inspirations.

15. A device according to claim 9, further comprising a device for generating the hemodynamic-related signal, wherein the respiration sensor is in fluid communication with a connector for connecting a measurement hose.

16. A device according to claim 9, wherein said variance corresponds to a variability of sizes of said successive inspirations in a given time span, said comparison of said variance of said size of inspiration with said threshold providing an indication as to whether an accurate cardiovascular function is obtainable from said respiration-related signal and said hemodynamic-related signal.

17. A method of providing an indication of cardiovascular function, the method comprising the steps of:
    receiving a respiration-related signal indicative of a physical property of respiration gases administered to a patient;
    receiving a hemodynamic-related signal indicative of a hemodynamic property;
    processing the respiration-related signal to detect times of inspiration and a measure of the size of the inspiration;
    determining a variance in the size of inspiration of successive inspirations; comparing the variance of the size of inspiration with a threshold;
    correlating the sizes of inspiration with the hemodynamic-related signal, to obtain the indication of cardiovascular function only if said variance exceeds said threshold;
    providing a processor system and a computer program product comprising instructions for causing the processor system to perform the steps of receiving the respiration-related signal, receiving the hemodynamic-related signal, processing the respiration-related signal and correlating the sizes of inspiration with the hemodynamic-related signal.

18. A method according to claim 17, wherein said variance corresponds to a variability of sizes of said successive inspirations in a given time span, wherein said comparison of said variance of said size of inspiration with said threshold provides an indication as to whether an accurate cardiovascular function is obtainable from said respiration-related signal and said hemodynamic-related signal.

19. A method according to claim 17, wherein said variance corresponds to a maximal difference between any two sizes or a standard deviation of said sizes of inspiration of said successive inspirations.

* * * * *